United States Patent [19]

Deeba et al.

[11] Patent Number: 4,918,233
[45] Date of Patent: Apr. 17, 1990

[54] PRODUCTION OF ETHYLENEDIAMINE FROM MONOETHANOLAMINE AND AMMONIA

[75] Inventors: Michel Deeba, Allentown; Michael E. Ford, Center Valley; Thomas A. Johnson, Orefield, all of Pa.

[73] Assignee: Air Products and Chemicals, Inc., Allentown, Pa.

[21] Appl. No.: 883,000

[22] Filed: Jul. 8, 1986

[51] Int. Cl.$^4$ .................. C07C 85/06; C07C 87/16
[52] U.S. Cl. ................................. 564/479; 564/511
[58] Field of Search ........................... 564/479, 511

[56] References Cited

U.S. PATENT DOCUMENTS

| 3,068,290 | 12/1962 | Lichtenberger et al. | 564/480 |
|---|---|---|---|
| 3,137,730 | 6/1964 | Fitz-William | 564/480 |
| 3,506,400 | 4/1970 | Eberly et al. | 423/328 |
| 3,766,184 | 10/1973 | Johansson et al. | 544/358 |
| 4,123,462 | 10/1978 | Best | 564/480 |
| 4,205,012 | 5/1980 | Parker et al. | 502/60 |
| 4,254,061 | 3/1981 | Weiger | 564/479 |
| 4,434,300 | 2/1984 | Deeba et al. | 564/479 |
| 4,436,938 | 3/1984 | Tompsett | 564/479 |
| 4,458,092 | 7/1984 | Deeba et al. | 564/479 |
| 4,547,591 | 10/1985 | Brennan et al. | 564/479 |
| 4,584,411 | 4/1986 | Johnson | 568/451 |
| 4,617,418 | 10/1986 | Ford et al. | 564/479 |
| 4,737,592 | 4/1988 | Abrams et al. | 564/479 |

FOREIGN PATENT DOCUMENTS

| 180983 | 5/1986 | European Pat. Off. |
| 111670 | 9/1978 | Japan . |

OTHER PUBLICATIONS

Restelli, Jr., et al., *Transmethylation Reactions of Monomethyl and Dimethylamine Over Montmorillonite in a Flow System*, A.I. Ch. E. Journal, 12:292(1966).

Primary Examiner—Richard L. Raymond
Assistant Examiner—K. Konstas
Attorney, Agent, or Firm—Russell L. Brewer; James C. Simmons; William F. Marsh

[57] ABSTRACT

This invention relates to a process for producing ethylene diamine in high selectivity and high conversion by reacting monoethanolamine with ammonia in the presence of a catalyst. The catalyst which permits the production of ethylenediamine in high selectivity and high conversion is a hydrogen mordenite catalyst that has been treated in such a manner as to raise the silicon to aluminum ratio of the mordenite, such treatment, then being referred to as partial dealumination.

5 Claims, No Drawings

PRODUCTION OF ETHYLENEDIAMINE FROM MONOETHANOLAMINE AND AMMONIA

TECHNICAL FIELD

This invention relates to a process for producing ethylenediamine by reacting monoethanolamine with ammonia in the presence of a catalyst.

BACKGROUND OF THE INVENTION

Ethylenediamine is a composition well known in the industry and is used in a wide variety of applications. These applications for ethylenediamine include utility as chelating agents and surfactants, fabric softeners, lubricating oil additives, rubber accelerators, fungicides, insecticides, synthetic waxes, asphalt wetting agents and resinous polymers. In view of the wide utility of ethylenediamine, there has been substantial work done in the preparation of ethylenediamine which involves the reaction of ethylene oxide with ammonia, monoethanolamines with ammonia, or ethylene glycol with ammonia. The processes are catalytic and objectives of the processes have been to maximize conversion of the organic substrate with ammonia to form ethylenediamine and to maximize selectivity. Another approach to the preparation of ethylenediamine has involved the reaction of ethylene dichloride with ammonia but such process has numerous drawbacks because of the production of by-product sodium chloride and also because of the cost of corrosion-resistant equipment for such process.

Representative art showing the manufacture of ethylenediamine as well as other amines is shown on the following U.S. patents:

U.S. No. 3,068,290 discloses a process producing ethylenediamine by reacting monoethanolamine or ethylene oxide in the presence of catalysts, which by and large are hydrogenation catalysts such as Raney nickel, cobalt, reduced nickels, copper chromite, platinimum, osmium, palladium and the like either alone or on a supporting medium. Such catalysts have been combined with alkaline earth metal oxides such as magnesium oxide which enhance activity and increase selectivity.

U.S. No. 3,137,370 discloses the manufacture of ethylenediamine utilizing a hydrogenation catalyst comprising nickel and copper with the reaction carried out in the presence of water.

U.S. No. 3,766,184 discloses the preparation of ethylenediamine by reacting monoethanolamine and ammonia in the presence of an amination catalyst comprising iron, nickel or cobalt.

U.S. No. 4,123,462 discloses amination processes using nickel-rhenium catalysts as the catalyst.

Catalytic processes have been used for the manufacture of alkylamines and diamines such as methylamines, ethylamines and, and general $C_1$ to $C_6$ alkylamines. Representative patents show the amination of alkanols to produce alkylamines including methylamines, etc. as set forth in the following patents:

U.S. No. 4,458,092 cites a number of patents which disclose processes for the manufacture of amines by the reaction of alcohol and ammonia in the presence of zeolites. The zeolites used in this patent for producing methylamines in high selectivity were rare earth Y zeolite and hydrogen exchanged Y zeolite.

U.S. No. 4,436,938 discloses a process for producing methylamines by reacting methanol or dimethylether with ammonia over a binderless zeolite A catalyst. The zeolite being exchanged with various cations such as sodium, calcium, magnesium, cerium and lanthanum.

U.S. No. 4,434,300 discloses a process for producing methylamines by reacting methanol with ammonia using macroporous highly acidic alumino-silicates. Microporous hydrogen-chabazite-erionite was the preferred catalyst.

U.S. No. 4,254,061 discloses a catalytic process for producing monomethylamine by reacting methanol and ammonia over a catalyst selected from the group of mordenite, ferrierite, erionite, and clinoptilolite. Specific cations are suggested for each zeolite system.

U.S. No. 4,205,012 discloses the manufacture of amines by reacting an alcohol with ammonia in the presence of a zeolite and particularly the zeolite designated FU-1. The catalytic process produces mono and dimethylamine in preference to trimethylamine.

SUMMARY OF THE INVENTION

This invention relates to an improvement in a basic process involving the reaction of ammonia with monoethanolamine to produce ethylenediamine. The improvement constituting the basis of this invention involves the utilization of a dealuminated rare earth or hydrogen ion exchanged mordenite as the catalyst.

A significant advantage afforded by the utilization of a rare earth exchanged or hydrogen exchanged mordenite zeolite is that the process is extremely effective in producing ethylenediamine in high conversion while at the same time being highly selective to ethylenediamine with low by-product formation. This is in contrast to many of the prior art processes utilizing hydrogenation catalysts which sacrificed selectivity to ethylenediamine in favor of conversion.

DETAILED DESCRIPTION OF THE INVENTION

The basic process for producing ethylenediamine involves contacting monoethanolamine with ammonia at elevated temperature in the presence of a catalyst. The mole ratio of ammonia to monoethanolamine ranges from stoichiometric (1:1) to about 16 moles of ammonia per moles of monoethanolamine. (If ethylene glycol is substituted for monoethanolamine, it is assumed that conditions are appropriate for first converting ethylene glycol to monoethanolamine and that the monoethanolamine thus produced is converted on contact with ammonia to ethylenediamine.) Greater molar excesses of ammonia to monoethanolamine can be used; however, no significant advantage accrues from their use. Temperatures for carrying out the reaction between ammonia and monoethanolamine range from 250° to 350° C. Pressures range from about 25 to 1000 psig for continuous reactions, and from about 200 to 5000 psig for batch reactions. The reaction time ranges from about 1 to 6 hours if the reaction is carried in a batch reactor. For continuous reactions, space velocities expressed as liquid hourly space velocity (LHSV) of from 0.05 to 5 hours$^{-1}$ (based on monoethanolamine).

The key to obtaining high conversion of monoethanolamine to ethylenediamine and at high selectivity, is the specific catalyst used in the process. The catalyst is a partially dealuminated rare earth exchanged or hydrogen exchanged mordenite; i.e., a mordenite having some alumina extracted from the crystalline silica-alumino framework. The catalyst is rendered acidic by exchanging the cation in the mordenite, typically sodium, with a rare earth metal or hydrogen. Of these, hydrogen is preferred, although of the rare earth metals, lanthanum is preferred. Other examples of rare earth metals which can be used include neodymium, praseodymium and yttrium. Exchanging the mordenite with rare earth metal ion or hydrogen ion substantially increases the acidity of the catalyst and makes it much more reactive for amination of monoethanolamine. In addition, partial dealumination leads to greater catalytic activity by improving the diffusivity of reactants into, and products out of the mordenite structure.

By partial dealumination it is meant that the mordenite is treated with a dealuminating agent, such as a chelating agent, acid, or other treatment for the purpose of removing aluminum atoms from the zeolite structure. Typically, 10% to 90% of the total alumina present in the mordenite is removed to provide a desired Si to Al molar ratio. Mordenite normally has Si to Al molar ratio to about 5:1 and a partially dealuminated mordenite would have an Si to Al molar ratio of about 6-100:1 and preferably from about 6.5-15:1.

There are several techniques available for removing aluminum atoms from the mordenite structure and some involve the treatment of the mordenite with a chelating agent such as acetyl acetonate or ethylenediamine tetracetic acid, a treatment with a mineral acid, e.g., hydrochloric acid or by activation using silicon tetrachloride. Examples of various techniques for removing aluminum atoms from zeolite materials including mordenites, are noted in U.S. No. 3,506,400; U.S. No. 3,937,791; and U.S. No. 3,761,396; these techniques are incorporated by reference.

The following examples are provided to illustrate various embodiments and permit one to provide comparisons with other catalytic systems and preparation of ethylenediamines. The examples are not intended to be restrictive of the invention.

EXAMPLE 1

Preparation of Dealuminated Mordenite of Various Si; Al Mole Ratios

A mixture of Norton Z-900H (1/16" extrudates) hydrogen mordenite (150 gms, silicon/aluminum (Si:Al) ratio is 6:1), 37% aqueous hydrochloric acid (5 ml), and deionized water (2 liter) was heated under reflux for 1 hour. The H-form of the mordenite was used in preference to the Na form as contact with HCl to exchange the ion and dealuminate sometimes adversely affects the crystalline structure of the Na form. Therefore, it is preferred to convert the mordenite to the H form using an ammonium salt and heat prior to dealumination. After cooling and filtration, the catalyst was washed with deionized water (2 liter) under reflux for 1 hour. Filtration and drying provided a zeolite catalyst with a silicon/aluminum molar ratio of 6.3. Hereafter, this catalyst is designated as "Catalyst A".

A portion of Catalyst A prepared above (75 gms) was treated with 37% aqueous hydrochloric acid (15 ml), and deionized water (1 liter) and heated under reflux for 1 hour. After cooling and filtration, the catalyst was washed with deionized water (2 liter) at reflux for 1 hour. Filtration and drying provided a zeolite catalyst with an Si:Al molar ratio of 7.2. Hereafter, this catalyst is designated as "Catalyst B".

A mixture of Norton Z-900H hydrogen mordenite (80 gm), 37% aqueous hydrochloric acid (50 ml), ammonium chloride (110 gms); and deionized water (1.5 liter) was heated under reflux for 1 hour. (The increased amount of HCl was intended to increase dealumination.) After cooling and filtration, the catalyst was washed with deionized water (2 liter) at reflux temperature for 1 hour. The mixture was then filtered and the dealuminated mordenite dried and a zeolite catalyst with a silica/alumina molar ratio of 9.2 was obtained. Hereafter, the catalyst is designated as "Catalyst C".

The above procedure was repeated, with the dealumination step being carried out with 2 liters of deionized water, instead of the original 1.5 liter. A catalyst with a molar silica/alumina ratio of 6.9 was obtained. Hereafter, this catalyst is designated as "Catalyst D".

EXAMPLE 2

Batch Aminations of MELA With Catalyst

Several runs were made by mixing monoethanolamine, ammonia, and a catalyst was described and placing in a 300 ml stainless steel stirred autoclave. The mixture was heated to 300° C. for 4 hours, during which time autogeneous pressure of 2100–4900 psig developed. During the reaction, the mixture was stirred at 2000 rpm. Analysis of the cooled reaction mixture by gas-liquid chromatography indicated substantial conversion of MELA to predominately EDA. Tables 1 and 2 provide details of the reaction conditions and results.

TABLE 1

| | | | Batch Amination of MELA With Zeolite Catalysts | | | | | | | | | |
|---|---|---|---|---|---|---|---|---|---|---|---|---|
| Run | Moles MELA | Moles NH$_3$ | NH$_3$/MELA[a] | Catalyst (wt. %)[b] | Temp (°C.)[c] | Press Psig | Time (Hr) | Conv (%)[b] | Selectivity[d] | | | | |
| | | | | | | | | | EDA[e] | C[f] | NC[g] | AEEA[h] | UNK[i] |
| 1 | 1.03 | 2.06 | 2/1 | A (10.8) | 300 | 2150 | 4 | 21 | 57 | 0 | 0 | 43 | 0 |
| 2 | 1.03 | 2.06 | 2/1 | B (10.9) | 300 | 2300 | 4 | 17 | 61 | 0 | 0 | 39 | 0 |
| 3 | 0.77 | 3.02 | 3.9/1 | B (14.8) | 300 | 4860 | 4 | 15 | 84 | 0 | 0 | 16 | 0 |
| 4 | 0.78 | 3.00 | 3.8/1 | B (14.3) | 325 | 3660 | 4 | 26 | 80 | 1 | 4 | 15 | 0 |

Notes to Table 1:
[a]Mole ratio ammonia/MELA.
[b]Based on MELA.
[c]Maximum pressure attained during reaction.
[d]Feedstock-free, water-free, weight-normalized basis.
[e]Weight percent of EDA in total product.
[f]Weight percent of cyclic polyamines in total product.
[g]Weight percent of higher noncyclic polyamines in total product.
[h]Weight percent of aminoethylethanolamine in total product.
[i]Weight percent unknowns in product.

TABLE 2

| | Product Distribution[a] | | | | | | |
|---|---|---|---|---|---|---|---|
| RUN | EDA[b] | PIP[c] | DETA[d] | AEEA[e] | C[f] | NC[g] | UNK[h] |
| 1 | 57.35 | 0 | 0 | 42.65 | 0 | 0 | 0 |
| 2 | 61.36 | 0 | 0 | 38.64 | 0 | 0 | 0 |

TABLE 2-continued

| | Product Distribution[a] | | | | | | |
|---|---|---|---|---|---|---|---|
| RUN | EDA[b] | PIP[c] | DETA[d] | AEEA[e] | C[f] | NC[g] | UNK[h] |
| 3 | 84.34 | 0 | 0 | 15.66 | 0 | 0 | 0 |
| 4 | 79.79 | 1.30 | 4.38 | 14.53 | 0 | 0 | 0 |

Notes to Table 2:
[a]Feedstock-free, water-free, weight-normalized basis
[b]Ethylenediamine
[c]Piperazine
[d]Diethylenetriamine
[e]Aminoethylethanolamine
[f]Higher cyclic polyamines
[g]Higher noncyclic polyamines
[h]Unknown components From Table 1 It can be noted that EDA is the major product of all batch reactions. However, best selectivities to EDA are obtained with an ammonia to MELA molar feed ratio of 4:1. The higer ammonia to MELA ratio favors amination of MELA to form EDA, rather than self-condensation of MELA to form aminoethylethanolamine. Conversion of MELA to EDA increased with increasing reaction temperature (compare Runs 3 and 4); however, selectivity to EDA did not significantly decrease at the higher conversions. This observation reflects operation of shape selectivity of the dealuminated H-mordenite catalyst for EDA production within the 300°–325° range. Moreover, the shape selectivity of the catalyst is shown by the virtually complete absence of cyclic products and higher polyamines such as DETA, TETA, and TEPA. With conventional rare earth metal hydrogen phosphate catalysts under these conditions, higher concentrations of both cyclic and higher molecular weight polyamines are formed from MELA and ammonia with either 2:1 or 4:1 ammonia to MELA feeds. However, steric constraints on the amination process by the pore structure of the dealuminated mordenite catalyst prevent cyclization of aminoethylethanolamine to piperazine, and homologation of EDA to higher polyamines.

EXAMPLE 3

A series of amination reactions was carried out in a fixed bed catalytic reactor under various conditions using hydrogen mordenite and the dealuminated catalysts A, B, C, and D. These conditions and reaction product are set forth in Tables 3 and 4. Comparative Runs with amorphous silica-alumina and other zeolites are set forth in Tables 5 and 6.

TABLE 3

Continuous Amination of MELA With Zeolite Catalysts[a]

| Run | NH$_3$/MELA[b] | Catalyst | Temp (°C.) | LHSV (HR$^{-1}$)[c] | Conv (%)[c] | Selectivity[d] EDA[e] | C[f] | NC[g] | AEEA[h] | UNK[i] |
|---|---|---|---|---|---|---|---|---|---|---|
| 1 | 12 | H-Mordenite | 300 | 0.15 | 24 | 30 | 31 | 5 | 24 | 10 |
| 2 | 16 | H-Mordenite | 300 | 0.15 | 20 | 30 | 30 | 6 | 25 | 9 |
| 3 | 16 | A | 300 | 0.15 | 23 | 54 | 19 | 3 | 19 | 5 |
| 4 | 12 | B | 300 | 0.15 | 22 | 53 | 18 | 4 | 18 | 7 |
| 5 | 16 | B | 300 | 0.15 | 21 | 54 | 18 | 3 | 18 | 7 |
| 6 | 8 | D | 300 | 0.15 | 26 | 57 | 15 | 2 | 17 | 9 |
| 7 | 16 | D | 300 | 0.15 | 27 | 59 | 17 | 3 | 12 | 9 |
| 8 | 8 | D | 300 | 0.30 | 17 | 58 | 11 | 3 | 23 | 5 |
| 9 | 16 | D | 300 | 0.30 | 15 | 56 | 12 | 2 | 20 | 10 |
| 10 | 12 | H-Mordenite | 310 | 0.15 | 31 | 34 | 32 | 5 | 15 | 14 |
| 11 | 16 | H-Mordenite | 310 | 0.15 | 29 | 33 | 32 | 7 | 17 | 11 |
| 12 | 12 | B | 310 | 0.15 | 29 | 55 | 20 | 4 | 12 | 9 |
| 13 | 16 | B | 310 | 0.15 | 24 | 56 | 18 | 4 | 14 | 8 |
| 14 | 9 | D | 310 | 0.30 | 30 | 63 | 14 | 3 | 12 | 8 |
| 15 | 12 | D | 310 | 0.22 | 30 | 64 | 14 | 3 | 11 | 8 |
| 16 | 8 | C | 325 | 0.30 | 25 | 49 | 22 | 5 | 14 | 10 |
| 17 | 12 | C | 325 | 0.30 | 21 | 52 | 20 | 6 | 13 | 9 |
| 18 | 16 | C | 325 | 0.30 | 23 | 54 | 19 | 5 | 11 | 11 |
| 19 | 8 | C | 325 | 0.50 | 12 | 48 | 20 | 4 | 17 | 11 |
| 20 | 8 | D | 325 | 0.15 | 56 | 54 | 20 | 5 | 4 | 17 |
| 21 | 16 | D | 325 | 0.15 | 45 | 56 | 20 | 5 | 5 | 14 |
| 22 | 8 | D | 325 | 0.30 | 23 | 56 | 16 | 4 | 15 | 9 |
| 23 | 16 | D | 325 | 0.30 | 27 | 62 | 16 | 3 | 11 | 8 |

Notes to Table 3:
[a]All reactions carried out at 150 psig.
[b]Mole ratio ammonia/MELA.
[c]Based on MELA
[d]Feedstock-free, water-free, weight-normalized basis; rounded off to nearest whole number.
[e]Weight percent of EDA in the total product.
[f]Weight percent of cyclic polyamines in the total product.
[g]Weight percent of higher noncyclic polyamines in the total product.
[h]Weight percent of aminoethylethanolamine in the total product.
[i]Weight percent of unknowns in the product.

TABLE 4

| | Product Distribution[a] | | | | | | | | | | |
|---|---|---|---|---|---|---|---|---|---|---|---|
| RUN | EDA[a] | PIP[b] | DETA[c] | TEDA[d] | AEEA[e] | AEP[f] | NCTETA[g] | CTETA[h] | NCTEPA[i] | CTEPA[j] | UNK[k] |
| 1 | 30.49 | 7.00 | 4.35 | 1.73 | 24.30 | 13.98 | 0.23 | 7.65 | 0 | 0.74 | 9.54 |
| 2 | 30.40 | 6.85 | 4.23 | 1.87 | 25.40 | 13.86 | 0.27 | 7.33 | 0 | 0.58 | 9.21 |
| 3 | 53.79 | 5.24 | 2.55 | 0.99 | 19.16 | 8.72 | 0 | 4.33 | 0 | 0 | 5.22 |
| 4 | 53.12 | 5.22 | 2.76 | 0.98 | 18.39 | 8.56 | 0.38 | 3.28 | 0 | 0.31 | 7.09 |
| 5 | 54.29 | 4.97 | 2.63 | 1.06 | 18.40 | 8.26 | 0.35 | 3.24 | 0 | 0.25 | 6.54 |
| 6 | 56.71 | 3.99 | 2.14 | 1.01 | 16.84 | 6.73 | 0.17 | 3.35 | 0.29 | 0.24 | 8.54 |
| 7 | 58.81 | 5.01 | 2.62 | 1.14 | 12.23 | 6.72 | 0.21 | 3.51 | 0.32 | 0.34 | 9.09 |
| 8 | 57.76 | 2.59 | 2.13 | 0.66 | 23.05 | 5.58 | 0.34 | 2.59 | 0 | 0 | 5.28 |
| 9 | 54.58 | 2.76 | 2.29 | 0 | 20.32 | 6.12 | 0 | 3.28 | 0 | 0 | 10.65 |
| 10 | 33.77 | 8.11 | 5.50 | 1.84 | 15.29 | 14.14 | 0.28 | 7.05 | 0 | 0.44 | 13.58 |

TABLE 4-continued

| RUN | EDA[a] | PIP[b] | DETA[c] | TEDA[d] | AEEA[e] | AEP[f] | NCTETA[g] | CTETA[h] | NCTEPA[i] | CTEPA[j] | UNK[k] |
|---|---|---|---|---|---|---|---|---|---|---|---|
| 11 | 33.15 | 8.01 | 5.46 | 2.13 | 17.35 | 14.53 | 0.40 | 7.28 | 0 | 0.53 | 11.16 |
| 12 | 54.63 | 6.48 | 3.99 | 1.07 | 12.36 | 9.07 | 0.25 | 3.15 | 0 | 0.17 | 8.82 |
| 13 | 55.96 | 5.58 | 3.29 | 0.98 | 14.18 | 8.58 | 0.18 | 2.95 | 0 | 0.23 | 8.07 |
| 14 | 63.30 | 3.67 | 2.24 | 0.91 | 12.43 | 5.82 | 0.23 | 2.96 | 0 | 0.31 | 8.13 |
| 15 | 63.93 | 4.27 | 2.71 | 0.92 | 10.59 | 6.12 | 0.11 | 2.92 | 0.26 | 0.23 | 7.94 |
| 16 | 48.53 | 7.33 | 4.62 | 1.57 | 13.77 | 9.09 | 0.75 | 3.02 | 0.41 | 0.98 | 9.93 |
| 17 | 52.36 | 7.22 | 4.62 | 0.98 | 12.67 | 8.77 | 0.30 | 2.40 | 0 | 0.25 | 9.44 |
| 18 | 53.99 | 7.27 | 4.52 | 0.97 | 10.89 | 8.12 | 0.34 | 2.45 | 0.23 | 0.43 | 10.79 |
| 19 | 47.61 | 6.09 | 3.82 | 0.96 | 17.27 | 8.78 | 0.45 | 2.80 | 0 | 1.54 | 10.69 |
| 20 | 54.39 | 6.79 | 5.19 | 1.67 | 3.63 | 7.11 | 0.32 | 3.59 | 0.37 | 0.42 | 16.53 |
| 21 | 55.52 | 7.21 | 5.01 | 1.50 | 5.07 | 7.65 | 0.14 | 3.17 | 0.27 | 0.29 | 14.15 |
| 22 | 55.86 | 4.55 | 2.95 | 1.13 | 14.65 | 7.53 | 0.19 | 3.10 | 0.55 | 0.18 | 9.31 |
| 23 | 61.60 | 4.75 | 3.17 | 0.99 | 10.89 | 6.89 | 0.17 | 2.71 | 0.22 | 0.20 | 8.40 |

Notes to Table 3:
[a]Ethylenediamine
[b]Piperazine
[c]Diethylenetriamine
[d]Triethylenediamine
[e]Aminoethylethanolamine
[f]Aminoethylpiperazine
[g]Triethylenetetramine (noncyclic isomers)
[h]Triethylenetetramine (cyclic isomers)
[i]Tetraethylenepentamine (noncyclic isomers)
[j]Tetraethylenepentamine (cyclic isomers)
[k]Unknowns

TABLE 5

Continuous Amination of MELA With Acidic Catalysts[a]

| Comparative Run | NH$_3$/MELA[b] | Catalyst | Temp (°C.) | LHSV (HR-1)[c] | Conv (%)[c] | Selectivity | | | | |
|---|---|---|---|---|---|---|---|---|---|---|
| | | | | | | EDA[e] | C[f] | NC[g] | AEEA[h] | UNK[i] |
| 1 | 16 | Silica—Alumina | 275 | 0.15 | 40 | 8 | 37 | 8 | 10 | 37 |
| 2 | 12 | LZY-62 | 300 | 0.15 | 37 | 7 | 40 | 5 | 12 | 36 |
| 3 | 16 | LZY-62 | 300 | 0.15 | 37 | 8 | 43 | 3 | 14 | 32 |
| 4 | 12 | Silica-Alumina | 300 | 0.15 | 73 | 10 | 32 | 11 | 1 | 46 |
| 5 | 16 | Silica-Alumina | 300 | 0.15 | 73 | 10 | 34 | 12 | 1 | 43 |
| 6 | 16 | H-Clinoptilolite | 300 | 0.15 | 28 | 11 | 43 | 10 | 18 | 18 |
| 7 | 12 | SK-500 | 300 | 0.15 | 51 | 12 | 37 | 8 | 6 | 37 |
| 8 | 16 | SK-500 | 300 | 0.15 | 46 | 13 | 37 | 7 | 7 | 36 |

Notes to Table 4:
[a]All reactions carried out at 150 psig.
[b]Mole ratio ammonia/MELA.
[c]Based on MELA.
[d]Feedstock-free, water-free, weight-normalized basis; rounded off to nearest whole number.
[e]Weight percent of EDA in the total product.
[f]Weight percent of cyclic polyamines in the total product.
[g]Weight percent of higher noncyclic polyamines in the total product.
[h]Weight percent of aminoethylethanolamine in the total product.
[i]Weight percent of unknowns in the product.

TABLE 6

Product Distribution[a]

| COMP RUN | EDA[a] | PIP[b] | DETA[c] | TEDA[d] | AEEA[e] | AEP[f] | NCTETA[g] | CTETA[h] | NCTEPA[i] | CTEPA[j] | UNK[k] |
|---|---|---|---|---|---|---|---|---|---|---|---|
| 1 | 8.13 | 9.09 | 6.16 | 0.97 | 10.29 | 15.36 | 0.13 | 10.26 | 0.95 | 1.46 | 37.19 |
| 2 | 7.47 | 8.61 | 2.79 | 2.15 | 11.94 | 12.84 | 0.52 | 13.21 | 0.77 | 3.58 | 36.11 |
| 3 | 7.85 | 8.98 | 2.55 | 2.54 | 13.80 | 13.48 | 0.64 | 13.84 | 0.60 | 3.97 | 31.74 |
| 4 | 9.51 | 10.90 | 10.30 | 1.14 | 1.49 | 12.51 | 0.38 | 7.19 | 0.29 | 0.63 | 45.87 |
| 5 | 10.00 | 11.88 | 11.75 | 1.32 | 1.23 | 12.99 | 0.57 | 6.52 | 0.28 | 0.83 | 42.62 |
| 6 | 10.60 | 11.71 | 8.61 | 2.76 | 18.31 | 19.17 | 0.47 | 8.89 | 0.84 | 0.47 | 18.17 |
| 7 | 12.07 | 11.86 | 7.30 | 1.71 | 6.03 | 14.74 | 0.32 | 7.77 | 0.35 | 0.97 | 36.88 |
| 8 | 12.65 | 11.69 | 7.16 | 2.16 | 6.79 | 14.17 | 0.38 | 7.68 | 0.16 | 1.04 | 36.11 |

Notes to Table 4:
[a]Ethylenediamine
[b]Piperazine
[c]Diethylenetriamine
[d]Triethylenediamine
[e]Aminoethylethanolamine
[f]Aminoethylpiperazine
[g]Triethylenetetramine (noncyclic isomers)
[h]Triethylenetetramine (cyclic isomers)
[i]Tetraethylenepentamine (noncyclic isomers)
[j]Tetraethylenepentamine (cyclic isomers)
[k]Unknowns From the series of reactions reported in Tables 3–6, it should be noted that the comparative examples clearly show that hydrogen-exchanged mordenites, and especially dealuminated mordenites, are required for selective amination of MELA to form EDA. Attempts to aminate MELA with an amorphous silica-alumina proceed with high conversion; however, selectivity to EDA is poor (see comparative runs 1, 4, and 5). Amorphous silica-alumina possesses no regular intracrystalline pore structure. Consequently, reaction occurs only on its surface, and no shape selectivity is observed. When a small pore zeolite (hydrogen exchanged clinoptilolite; comparative run 6) was used, a low conversion of MELA was obtained. However, despite the low conversion of MELA, selectivity to EDA was not better than that obtained with amorphous silica-alumina. Apparently, owing to the small pores (4.4 Å diameter), MELA is not aminated within the clinoptilolite structure. Only surface reaction, which is not subject to steric control by the zeolite, occurs. Conversely, use of large pore zeolites, e.g., hydrogen exchanged Y zeolite (comparative runs 2 and 3) and rare earth exchanged Y zeolite (comparative Runs 7 and 8) provided improved conversions. Selectivities to EDA remained low, owing to the lack of steric constraints on MELA amination by the open Y zeolite intracrystalline structure. In contrast to the catalysts examined in the comparative runs, hydrogen exchanged mordenite provided better selectivities to EDA at similar conversions (compare runs 1, 2, 10 and 11 with Comparative Runs 2, 3, and 6). In general, the best selectivities to EDA were obtained with dealuminated hydrogen mordenites (Runs 3-9, 12-23). Although good selectivities to EDA were obtained with all of the dealuminated hydrogen exchanged mordenites, moderately dealuminated mordenite (Catalyst D) was the most selective (Runs 14, 15, and 23). With dealuminated mordenites, selectivity to EDA was insensitive to conversion (compare Runs 6 and 7 with 20 and 21; runs 4 and 5 with 12 and 13; and Runs 8 and 9 with 22 and 23, respectively). As in the batch amination of MELA, this observation derives from steric control of MELA amination by the dealuminated mordenite catalysts within the 300°-325° range. In addition, with molar feed ratios of at least 8:1 ammonia:MELA, selectivities to EDA are insensitive to the ammonia:MELA feed ratio. However, inclusion of high concentrations of ammonia did no compensate for the lack of catalyst shape selectivity (e.g., compare runs 1 and 2 with 4 and 5; runs 10 and 11 with 12 and 13; runs 4 and 5 with comparative runs 2 and 3; and runs 3, 5, or 7 with comparative run 6).

To summarize, alcohol amination requires acidic materials to perform the reaction. The higher the acidity of the material, in terms of the number and strengths of acidic sites in a zeolitic catalyst, the higher should be the rate for alcohol amination.

The complete description of surface acidic properties of a solid with high surface area must involve the determination of the acid strength $H_o$, the density, the nature and the position of acidic sites. However, the surface heterogeneity complicates the measuring of acidic distribution and its correlation with catalytic activity. Thus, a comparison of the acidity and activity properties of different materials is not straightforward due to the absence of a quantitative model for relating the physicochemical properties of different surfaces.

Therefore, an ammonia adsorptivity procedure which gives the distribution of acid sites as a function of temperature was chosen for evaluating the acidity of a catalyst surface. It has been discovered that a material which shows high ammonia adsorptivity and therefore high acidity does not, by itself, mean it is a good catalyst for monoethanolamine amination.

The ammonia adsorptivity procedure which was used for measuring the acidity of solid surfaces is the following:

Acidity distribution was measured using a thermal gravimetric analysis technique with ammonia as the adsorbate. The acidity measurement was performed by activating about 20 to 40 mg of a catalyst at temperatures up to 400° C. in helium after which the catalyst was cooled to 25° C. The catalyst was then exposed to ammonia. The uptake of ammonia by the catalyst was very fast and the catalyst surface was saturated within five minutes.

Helium was then used to desorb the physically absorbed ammonia at 25° C. followed by desorption by heating the catalyst to 100°, 200°, 300° and 400° C., respectively. The temperature was raised to the next level after there was no change in the rate of desoprtion as indicated by decreasing weight of the catalyst. The amount of irreversibly adsorbed ammonia at each temperature was taken as a count of acidic sites. The amount of irreversibly adsorbed ammonia at 25° and 100° C. was considered as a measurement of total acidity (both weakly and strongly acidic sites) and the amount of ammonia irreversibly adsorbed at 200° and 300° C. as a measurement of strongly acidic sites. The strongly acidic sites are believed to be the important locals for the amination reaction.

Table 7 shows the acidity values of various zeolite catalyst in terms of millimoles of irreversibly adsorbed ammonia per gram of catalyst at the designated temperatures. As one characteristic of the dehydrated zeolitic catalysts suitable for practicing the process of this invention, the catalyst should be able to irreversibly adsorb at least 0.3 mmole ammonia, preferably 0.8 mmole ammonia, per gram of catalyst at 200° C.

Acidity measurement of a catalyst using a small molecule like ammonia as an adsorbate would be misleading if it is to be the sole basis for predicting activity and selectivity. An additional limiting factor for catalytic activity and selectivity over zeolites is possibly the critical diameter of the reactant and/or product molecules. Only those molecules that can pass through the zeolitic intracrystalline pores would be reacted or formed.

Microporous diffusivity, therefore, has great significance in catalytic reactions over zeolites. Accordingly, it is believed that some combination of or balance between the acidity and microporous diffusivity of the catalyst contributes to the conversion and selectivity for the amination of monoethanolamine.

However, the pores of some aluminosilicates (such as HY zeolite and amorphous silica alumina) are relatively large. Consequently, not only ethylenediamine and monoethanolamine, but also cyclic, branched, and linear dimeric and trimeric polyethylene amines can pass through the catalyst structure. Although conversion of MELA by such catalysts is high, selectivity to EDA is low, owing to the lack of steric constraints about the acidic amination site. Conversely, the pores of some zeolites (clinoptilolite) are relatively small. As a result, neither ethylenediamine and monoethanolamine, nor any of the cyclic, branched, and linear dimeric and trimeric polyethylene amines can pass through the catalyst structure. Conversion of monoethanolamine by such catalysts occurs only on the catalyst surface, with the degree of conversion being directly related to the surface area of the catalyst. However, selectivity to ethylenediamine is low, owing to the lack of steric constraints about the acidic amination sites on the catalyst surface. Consequently, to attain good selectivity to EDA, zeolitic intracrystalline pores should be large enough to allow ready diffusion of EDA, MELA, and ammonia, but small enough to hinder diffusion of dimeric and trimeric linear, branched, and cyclic polyethylene amines.

Ammonia, monoethanolamine and ethylenediamine have a critical diameter that required intracrystalline pore channels of at least about 5 Angstroms diameter to allow for their diffusion through the catalyst. To maintain good selectivity to EDA vs higher polyethylene amines, these intracrystalline pore channels should be between at least about 4A and 8A in diameter, and preferably between about 5A and 7A in diameter. Therefore, the crystalline aluminosilicates used in the process of this invention must meet this criterion. As indicated by Table 8, which shows the intracrystalline pore diameters of selected zeolites, mordenite and partially dealuminated mordenites have the preferred pore dimensions for shape selective amination of ethanolamine. Inclusion of Table 8, however, is not intended to limit the scope of this reaction.

TABLE 7

Irreversibly Adsorbed Ammonia (mmole/g Catalyst)

| Catalyst | Temperature (°C.) | | | | |
|---|---|---|---|---|---|
| | 25 | 100 | 200 | 300 | 400* |
| H-mordenite | 3.8 | 2.2 | 1.4 | 0.98 | — |
| REY Zeolite | 3.3 | 1.8 | 0.9 | 0.4 | — |
| H-Y Zeolite | 3.6 | 2.3 | 1.2 | 0.5 | — |
| Silica—Alumina (Amorphous) | 0.3 | 0.09 | Trace | — | — |
| Dealuminated H-mordenite | 3.7 | 2.1 | 1.36 | 0.89 | — |

*At 400° C. ammonia desorption was complete.

TABLE 8

| Zeolite | Channel System$^a$ (Å) | Type of Channels (Dimensions) | Face Dimension of Cavities$^b$ (Å) | Si:Al Ratio$^c$ |
|---|---|---|---|---|
| Erionite | 3.6 × 5.2 | 3 | 6.3 × 13.0 | 3–3.5 |
| Chabazite | 3.6 × 3.7 | 3 | 6.5 × 11.0 | 1.6–3.0 |
| Mordenite | 6.7 × 7.0 | 1 | — | 4.5–5.0 |
| | 2.9 × 5.7 | 1 | — | |
| A | 4.1 | 3 | 11.4 | 1.0 |
| X | 7.4 | 3 | 11.8 | 1.2 |
| Y | 7.4 | 3 | 11.8 | 2.5 |
| ZSM-5 | 5.4 × 5.6 | 3 | — | 6 |
| | 5.1 × 5.5 | | | |
| Silica—Alumina | Amorphous | | | |

$^a$Meier and Olson, Atlas of Zeolite Structure Type, 1978.
$^b$Bauer, R. M., Molecular Sieves, Adv. Chem. Ser., ACS, 121,1 (1978).
$^c$Breck, D. W., Zeolite Molecular Sieves, John Wiley & Sons, 1974.

What is claimed is:

1. In a continuous process for producing ethylenediamine by contacting monoethanolamine with ammonia under conditions sufficient to effect condensation therebetween, said contacting being carried out in the presence of a catalyst, the improvement which comprises:
   carrying out the reaction in a fixed bed catalytic reactor at a pressure of from 25–1,000 psig; and
   utilizing as said catalyst a mordenite exchanged with a rare earth metal or hydrogen ion and said mordenite being dealuminated mordenite.

2. The process of claim 1 wherein said mordenite has a silicon to aluminum ratio of from 6.5:1 to 15:1.

3. The process of claim 2 wherein said mordenite is exchanged with a hydrogen ion.

4. The process of claim 3 wherein the mole ratio of monoethanolamine to ammonia is from 1:1–16.

5. The process of claim 4 wherein the reaction is carried out using a temperature of 250° C., and an LHSV of 0.05 to 5 hours$^{-1}$.

* * * * *